(12) United States Patent
Wu et al.

(10) Patent No.: US 9,944,670 B2
(45) Date of Patent: Apr. 17, 2018

(54) GEMCITABINE DERIVATIVES, COMPOSITIONS COMPRISING SAME AND PHARMACEUTICAL APPLICATIONS THEREOF

(71) Applicants: HANGZHOU MINSHENG INSTITUTES FOR PHARMA RESEARCH CO., LTD, Hangzhou, Zhejiang (CN); Hangzhou Yuanchang Medical Sci-Tech Co., Ltd, Hangzhou, Zhejiang (CN)

(72) Inventors: Yaodong Wu, Zhejiang (CN); Jiaqi Shan, Zhejiang (CN); Ximing Shen, Zhejiang (CN); Chunxia Wu, Zhejiang (CN); Binnan Huang, Zhejiang (CN)

(73) Assignees: HANGZHOU YUANCHANG MEDICAL SCI-TECH CO., LTD, Hangzhou, Zhejiang (CN); HANGZHOU MINSHENG INSTITUTES FOR PHARMA RESEARCH CO., LTD, Hangzhou, Zhejiang (CN)

( * ) Notice: Subject to any disclaimer, the term of this patent is extended or adjusted under 35 U.S.C. 154(b) by 0 days.

(21) Appl. No.: 15/101,816

(22) PCT Filed: Dec. 4, 2014

(86) PCT No.: PCT/CN2014/093005
§ 371 (c)(1),
(2) Date: Jun. 3, 2016

(87) PCT Pub. No.: WO2015/081867
PCT Pub. Date: Jun. 11, 2015

(65) Prior Publication Data
US 2016/0304550 A1 Oct. 20, 2016

(30) Foreign Application Priority Data
Dec. 4, 2013 (CN) .......................... 2013 1 0646358

(51) Int. Cl.
*C07H 19/06* (2006.01)
*A61K 31/7068* (2006.01)
*C07H 1/00* (2006.01)

(52) U.S. Cl.
CPC ......... *C07H 19/06* (2013.01); *A61K 31/7068* (2013.01); *C07H 1/00* (2013.01)

(58) Field of Classification Search
CPC ....... C07H 19/06; C07H 1/00; A61K 31/7068
See application file for complete search history.

(56) References Cited

U.S. PATENT DOCUMENTS 8,563,741 B2 * 10/2013 Qian .............................. 544/331
2014/0235568 A1    8/2014 Song et al.

FOREIGN PATENT DOCUMENTS

| CN | 1693309 A | 11/2005 | | |
|---|---|---|---|---|
| CN | 101061131 A | 10/2007 | | |
| CN | 102432654 A | 5/2012 | | |
| FR | 2874016 | 2/2006 | | |
| WO | 2010/075542 | 7/2010 | | |
| WO | 2010/085377 | 7/2010 | | |
| WO | WO 2010085377 A2 | * 7/2010 | ............ | C07D 235/16 |
| WO | 2011/143593 | 11/2011 | | |
| WO | WO 2011143593 A1 | * 11/2011 | ............. | C07H 19/06 |

OTHER PUBLICATIONS

Guo et al., Cancer Chemotherapy and Pharmacology., vol. 48, No. 2, (Aug. 1, 2001), pp. 169-176.*
Dasari et al., Bioconjugate Chemistry, vol. 24, No. 1, (Jan. 16, 2013), pp. 4-8.*
International Search Report in PCT/CN2014/093005 dated Mar. 9, 2015.
Dasari et al. "H-Gemcitiabine: A New Gemcitabine Prodrug for Treating Cancer", Bioconjugate Chemistry, vol. 24, No. 1, Jan. 16, 2013, pp. 4-8.
Guo et al. "Targeted delivery of a peripheral benzodiazepine receptor ligan-gemcitabine conjugate to brain tumors in a xenograft model", Cancer Chemotherapy and Pharmacology, vol. 48, No. 2, Aug. 1, 2001, pp. 169-176.

(Continued)

*Primary Examiner* — Jonathan S Lau
(74) *Attorney, Agent, or Firm* — Greenberg Traurig, LLP; Fang Xie

(57) ABSTRACT

The invention provides gemcitabine derivatives shown in the following formula (I) and preparation methods thereof. The invention further relates to a pharmaceutical composition which comprising the said gemcitabine derivatives in an effective amount and a pharmaceutically acceptable excipient or additive. The invention further provides use of the said derivatives for preparing anti-tumor drugs. The compound designed by the invention is novel in structure and has a remarkable anti-tumor activity. According to the compound designed by the invention, the preparation starting materials have extensive sources and are easily obtained, the preparation method is simple and easy to operate, and the yield of the product is high, so that industrial production on a large scale is facilitated.

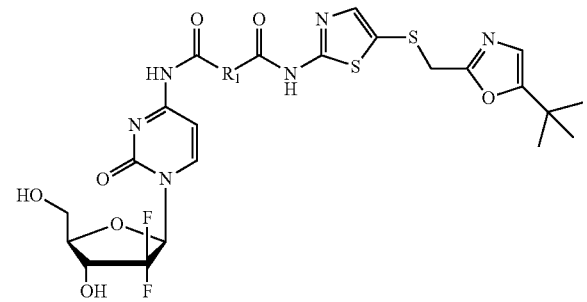

22 Claims, No Drawings

(56) References Cited

OTHER PUBLICATIONS

Rag et al. "N-(cycloalkylamino)acyl-2-aminothiazole inhibitors of cyclin-dependent kinase 2. N-[5-[[[5-(1, 1-dimethylethyl)-2-oxazolyl]methly]thio]-2-thi azolyl]-4-piperidinecarboxamide (BMS-387032), a highly efficacious and selective antitumor agent", Journal of Medicinal Chemistry, American Chemical Society, vol. 47, No. 7, Mar. 25, 2004, pp. 1719-1728.
Extended European Search Report for corresponding European Patent Application No. 14867802.2, dated May 4, 2017.

* cited by examiner

GEMCITABINE DERIVATIVES, COMPOSITIONS COMPRISING SAME AND PHARMACEUTICAL APPLICATIONS THEREOF

CROSS REFERENCE TO RELATED APPLICATIONS

This application is a national phase filing under 35 U.S.C. 371 of International Application No. PCT/CN2014/093005, filed Dec. 4, 2014, which claims priority to and the benefit of Chinese Patent Application No. CN 201310646358.7, filed Dec. 4, 2013, the disclosures of both of which are incorporated herein by reference in their entirety.

TECHNICAL FIELD

The present invention belongs to the field of medicine. Particularly, the present invention relates to a kind of gemcitabine derivatives, compositions comprising such derivatives and application of these derivatives for the manufacture of medicaments, especially medicaments for treating tumors.

TECHNICAL BACKGROUND

Tumor is a kind of disease with great threat to human health. Benefiting from technological advances of life science research, and in-depth understanding of tumor pathology in the last three decades, breakthrough on research and development of antitumor drugs were obtained. The successful development of various types of novel molecule targeted antitumor drugs has played an important role in improving tumor treatment levels. At present stage, the difficulty of tumor treatment is tumor drug resistance. Heterogeneity and easy mutation characteristics of tumor are the main reasons prone to drug resistance thereof, therefore, it is of great clinical significances to carry out drug research and development according to the mechanism of tumor drug resistance.

Antimetabolite drugs is an important part of antineoplastic drugs, whose market share accounted for 15.75% of the whole hospital antitumor drug market in 2010, ranking third. Antimetabolite antitumor drug is mainly composed of nucleoside drugs, wherein gemcitabine, cytarabine, decitabine, azacitidine, cladribine, fludarabine, nelarabine, etc. are most commonly used.

Gemcitabine is a fluorocytidine analogue, which belongs to cycle-specific antitumor drugs. Gemcitabine acts primarily on DNA synthetic phase, and it also can block the progress from DNA pre-synthetic stage to the DNA synthetic stage in cell cycle. Under the action of deoxycytidine kinase, gemcitabine is converted to the active gemcitabine diphosphate and triphosphate, which thereby inhibits tumor cell division and induces tumor cell apoptosis by affecting DNA synthesis and repair. Gemcitabine is suitable for the treatment of mid-stage and advanced non-small cell lung cancer, locally advanced or metastasized pancreatic carcinoma.

Gemcitabine can be used in the treatment of paclitaxel-resistant and anthraquinones-resistant breast cancer. Studies have shown that over-expression of resistance gene P-gp and MRP is an important reason that related drug resistant tumor cells are sensitive to gemcitabine, and the possible mechanism is that increased expression of deoxycytidine kinase caused by multidrug resistance can improve the accumulation of gemcitabine triphosphate (dFdCTP) in tumor cell, and promote the combination of gemcitabine to DNA strands in tumor cell, thereby increases the drug susceptibility of drug resistant tumor cells.

Current studies of gemcitabine and its derivatives mainly focus on synthesizing compounds of high anti-tumor activity through the modification and alteration on the amine group of cytosine ring. However, there is a shortcoming that it only aims at single-target effect on inhibiting DNA synthesis in tumor cell, multi-target mechanism is not considered to synthesize compounds with high anti-tumor activity because of the objective technical difficulty.

SUMMARY OF THE INVENTION

The present invention is quite different from the conventional gemcitabine modification or alteration strategies. Taking gemcitabine as a precursor compound, the synthesis strategy of multi-target and multi-mechanism acting synergistically while protecting the active pharmacophore of gemcitabine was induced, then new active groups targeting specific molecular were introduced through structural optimization, with the result that a class of gemcitabine-based compounds with novel structure and double-target inhibitory activity of CDK and DNA synthesis were prepared. In particular, the present invention can further improve the inhibitory activity against drug resistant tumor cell proliferation of gemcitabine-based compounds.

The present invention is realized by the following technical solutions:

The present invention provides a kind of gemcitabine derivatives with the following general formula I:

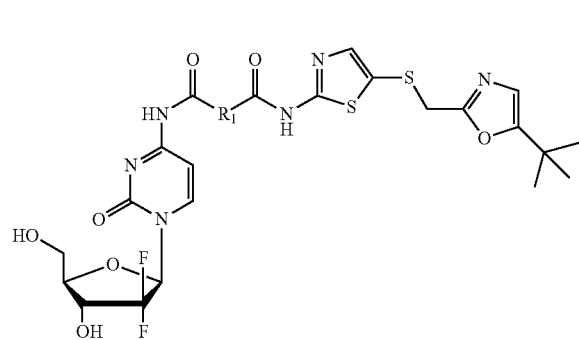

I

Wherein $R_1$ is selected from unsubstituted or substituted $C_{1-10}$ alkyl, unsubstituted or substituted $C_{2-10}$ alkenyl, unsubstituted or substituted $C_{2-10}$ alkynyl, unsubstituted or substituted $C_{3-7}$ cycloalkyl, unsubstituted or substituted $C_{3-7}$ cycloalkyloxy, wherein the said substituent is selected from one or more of halogen, cyano, nitro, amino, trifluoromethyl, thiol, hydroxyl, carboxyl, carbonyl, $C_{1-6}$ alkyl, $C_{2-6}$ alkenyl, $C_{2-6}$ alkynyl, $C_{1-6}$ alkoxy, $C_{1-6}$ alkoxycarbonyl and —NH—;

or $R_1$ is optionally substituted aryl, wherein the said substituent is selected from one or more of hydrogen, hydroxyl, carboxyl, nitro, halogen, $C_{1-6}$ alkyl and $C_{1-6}$ alkoxy.

Preferably, the optionally substituted aryl is phenyl, benzyl or naphthyl.

In one embodiment, $R_1$ is preferably selected from unsubstituted or substituted $C_{3-10}$ alkyl, unsubstituted or substituted $C_{3-10}$ alkenyl, unsubstituted or substituted $C_{3-10}$ alkynyl, unsubstituted or substituted $C_{3-7}$ cycloalkyl, unsubstituted or substituted $C_{3-7}$ cycloalkyloxy, or the optionally substituted aryl which is selected from phenyl, benzyl or naphthyl, wherein the said substituent is one or more of halogen, cyano, nitro, amino, trifluoromethyl, thiol, hydroxyl, carboxyl, carbonyl, $C_{1-6}$ alkyl, $C_{2-6}$ alkenyl, $C_{2-6}$ alkynyl, $C_{1-6}$ alkoxy, $C_{1-6}$ alkoxycarbonyl and —NH—.

Preferably, halogen is F, Cl, Br or I.

In another embodiment, $R_1$ is preferably selected from unsubstituted or substituted $C_{4-6}$ alkyl, unsubstituted or substituted $C_{4-6}$ alkenyl, unsubstituted or substituted $C_{4-6}$ alkynyl, unsubstituted or substituted $C_{3-7}$ cycloalkyl, unsubstituted or substituted $C_{3-7}$ cycloalkyloxy, the said substituent is selected from F and Cl.

The most preferred compounds of the present invention are named sequentially as number GI-01 to GI-09:

Number GI-01: N-(5-(((5-(t-butyl) oxazol-2-yl)methyl)thio)thiazol-2-yl)-N'-(1-((2R,4R,5R)-3,3-difluoro-4-hydroxy-5-(hydroxymethyl)tetrahydrofuran-2-yl)-2-oxo-1,2-dihydro-pyrimidin-4-yl)oxamide, Number GI-02: N-(5-(((5-(t-butyl) oxazol-2-yl)methyl)thio)thiazol-2-yl)-N'-(1-((2R,4R,5R)-3,3-difluoro-4-hydroxy-5-(hydroxymethyl)tetrahydrofuran-2-yl)-2-oxo-1,2-dihydro-pyrimidin-4-yl)malonamide, Number GI-03: N-(5-(((5-(t-butyl) oxazol-2-yl)methyl)thio)thiazol-2-yl)-N'-(1-((2R,4R,5R)-3,3-difluoro-4-hydroxy-5-(hydroxymethyl)tetrahydrofuran-2-yl)-2-oxo-1,2-dihydro-pyrimidin-4-yl)succinamide, Number GI-04: N-(5-(((5-(t-butyl) oxazol-2-yl)methyl)thio)thiazol-2-yl)-N'-(1-((2R,4R,5R)-3,3-difluoro-4-hydroxy-5-(hydroxymethyl)tetrahydrofuran-2-yl)-2-oxo-1,2-dihydro-pyrimidin-4-yl)glutaramide, Number GI-05: N-(5-(((5-(t-butyl) oxazol-2-yl)methyl)thio)thiazol-2-yl)-N'-(1-((2R,4R,5R)-3,3-difluoro-4-hydroxy-5-(hydroxymethyl)tetrahydrofuran-2-yl)-2-oxo-1,2-dihydro-pyrimidin-4-yl)adipamide, Number GI-06: N-(5-(((5-(t-butyl) oxazol-2-yl)methyl)thio)thiazol-2-yl)-N'-(1-((2R,4R,5R)-3,3-difluoro-4-hydroxy-5-(hydroxymethyl)tetrahydrofuran-2-yl)-2-oxo-1,2-dihydro-pyrimidin-4-yl)pimelamide, Number GI-07: N-(5-(((5-(t-butyl) oxazol-2-yl)methyl)thio)thiazol-2-yl)-N'-(1-((2R,4R,5R)-3,3-difluoro-4-hydroxy-5-(hydroxymethyl)tetrahydrofuran-2-yl)-2-oxo-1,2-dihydro-pyrimidin-4-yl)suberamide, Number GI-08: N-(5-(((5-(t-butyl) oxazol-2-yl)methyl)thio)thiazol-2-yl)-N'-(1-((2R,4R,5R)-3,3-difluoro-4-hydroxy-5-(hydroxymethyl)tetrahydrofuran-2-yl)-2-oxo-1,2-dihydro-pyrimidin-4-yl)azelamide, Number GI-09: N-(5-(((5-(t-butyl) oxazol-2-yl)methyl)thio)thiazol-2-yl)-N'-(1-((2R,4R,5R)-3,3-difluoro-4-hydroxy-5-(hydroxymethyl)tetrahydrofuran-2-yl)-2-oxo-1,2-dihydro-pyrimidin-4-yl)sebacamide.

The present invention also provides a method for preparing gemcitabine derivatives, comprising the steps as follows:

(1) In the presence of a condensing agent, mixing the following compounds of formula IV and formula V or formula VII to obtain the intermediate of formula III via amidation reaction, with the condition that, when the compound of formula IV reacts with compound of formula VII, Z is OH in the product compound of formula III. The reaction formula is as follows:

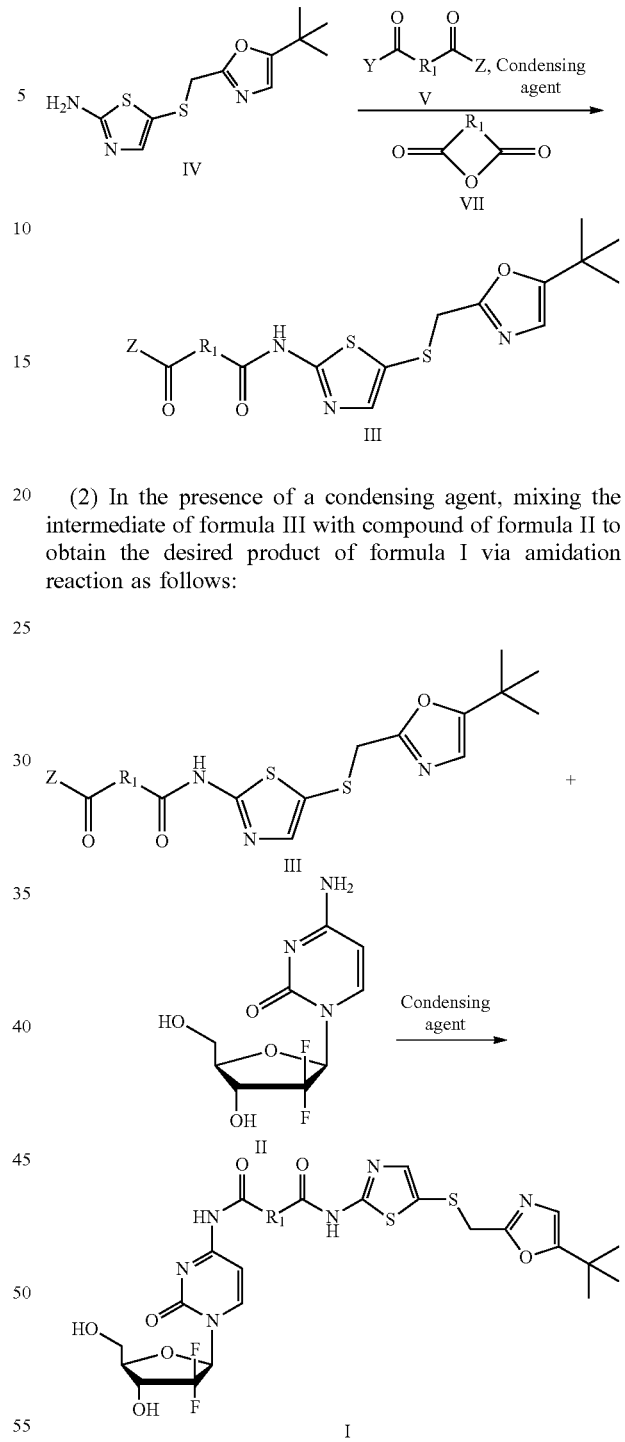

(2) In the presence of a condensing agent, mixing the intermediate of formula III with compound of formula II to obtain the desired product of formula I via amidation reaction as follows:

wherein, Y and Z each independently represents —OH, —F, —Cl, —Br or —I;

$R_1$ is selected from unsubstituted or substituted $C_{1-10}$ alkyl, unsubstituted or substituted $C_{2-10}$ alkenyl, unsubstituted or substituted $C_{2-10}$ alkynyl, unsubstituted or substituted $C_{3-7}$ cycloalkyl, unsubstituted or substituted $C_{3-7}$ cycloalkyloxy, wherein the said substituent is one or more of halogen, cyano, nitro, amino, trifluoromethyl, thiol, hydroxyl, carboxyl, carbonyl, $C_{1-6}$ alkyl, $C_{2-6}$ alkenyl, $C_{2-6}$ alkynyl, $C_{1-6}$ alkoxy, $C_{1-6}$ alkoxycarbonyl and —NH—; or $R_1$ is an optionally substituted aryl, wherein the said substituent is selected from one or more of hydrogen, hydroxyl, carboxyl, nitro, halogen, $C_{1-6}$ alkyl, $C_{1-6}$ alkoxy.

The reaction temperature of step (1) and step (2) is 0° C. to 150° C., preferably 20° C.-120° C.

The condensing agent of step (1) and step (2) is one or more of 1-hydroxybenzotriazole, 1-hydroxy-7-azo-benzotriazole, 3-hydroxy-1,2,3-benzotriazine-4(3H)-one, 1-ethyl-(3-dimethylaminopropyl)carbodiimide, N,N-dicyclohexyl carbodiimide, N,N-diisopropyl carbodiimide, preferably one or a combination of 1-hydroxybenzotriazole, 1-ethyl-(3-dimethylaminopropyl)carbodiimide, The reaction solvent of step (1) and step (2) is one or more of benzene, toluene, chloroform, n-hexane, cyclohexane, dichloromethane, 1,2-dichloroethane, methyl t-butyl ether, carbon tetrachloride, ethyl acetate, propyl acetate, butyl acetate, methanol, ethanol, acetone, tetrahydrofuran, diethyl ether, acetonitrile, N,N-dimethylformamide, dimethyl sulfoxide.

The present invention also provides another method for preparing gemcitabine derivatives, comprising the steps of:

(1) In the presence of a condensing agent, mixing the compound of formula II and formula V or formula VII to obtain the intermediate of formula VI via amidation reaction, with the condition that, when the compound of formula II reacts with compound of formula VII, Z is OH in the product compound of formula VI. The reaction formula is as follows:

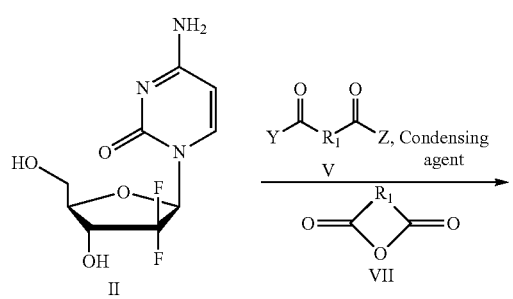

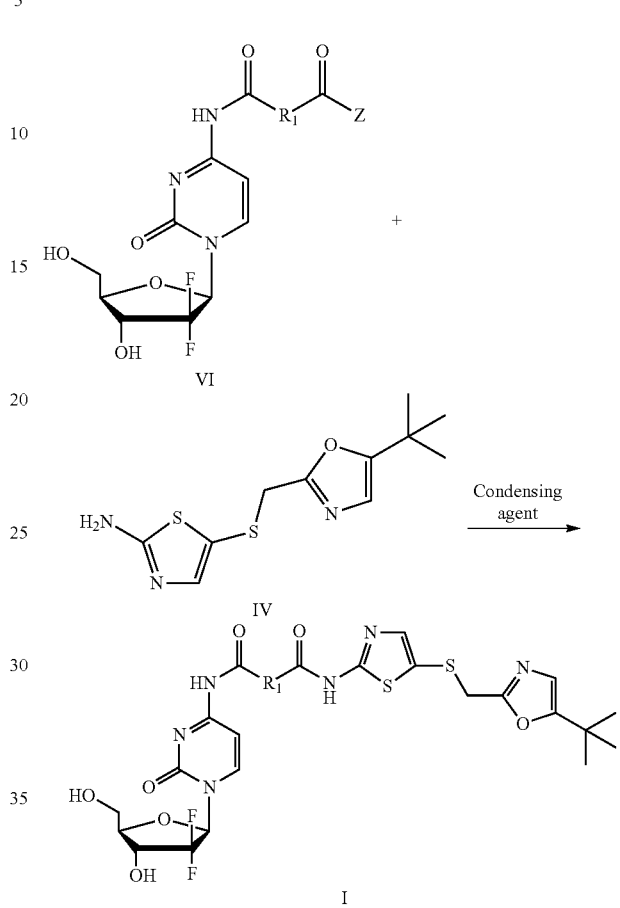

(2) In the presence of a condensing agent, mixing the intermediate of formula VI with compound of formula IV to obtain the desired product of formula I via amidation reaction as follows:

wherein, Y and Z each independently represents —OH, —F, —Cl, —Br or —I, $R_1$ is selected from unsubstituted or substituted $C_{1-10}$ alkyl, unsubstituted or substituted $C_{2-10}$ alkenyl, unsubstituted or substituted $C_{2-10}$ alkynyl, unsubstituted or substituted $C_{3-7}$ cycloalkyl, unsubstituted or substituted $C_{3-7}$ cycloalkyloxy, wherein the said substituent is one or more of halogen, cyano, nitro, amino, trifluoromethyl, thiol, hydroxyl, carboxyl, carbonyl, $C_{1-6}$ alkyl, $C_{2-6}$ alkenyl, $C_{2-6}$ alkynyl, $C_{1-6}$ alkoxy, $C_{1-6}$ alkoxycarbonyl and —NH—; or $R_1$ is an optionally substituted aryl, wherein the said substituent is selected from one or more of hydrogen, hydroxyl, carboxyl, nitro, halogen, $C_{1-6}$ alkyl, $C_{1-6}$ alkoxy.

The reaction temperature of step (1) and step (2) is 0° C. to 150° C., preferably 20° C.-120° C.

The condensing agent of step (1) and step (2) is one or more of 1-hydroxybenzotriazole, 1-hydroxy-7-azo-benzotriazole, 3-hydroxy-1,2,3-benzotriazine 4 (3H) one, 1-ethyl-(3-dimethylaminopropyl)carbodiimide, N,N-dicyclohexyl carbodiimide, N,N-diisopropyl carbodiimide, preferably one or a combination of 1-hydroxybenzotriazole, 1-ethyl-(3-dimethylaminopropyl)carbodiimide, The reaction solvent of step (1) and step (2) is one or more of benzene, toluene, chloroform, n-hexane, cyclohexane, dichloromethane, 1,2-dichloroethane, methyl t-butyl ether, carbon tetrachloride, ethyl acetate, propyl acetate, butyl acetate, methanol, ethanol, acetone, tetrahydrofuran, diethyl ether, acetonitrile, N,N-dimethylformamide, dimethyl sulfoxide.

In one embodiment, the condensing agent of step (1) and step (2) is one or a combination of 1-hydroxybenzotriazole, 1-ethyl-(3-dimethylaminopropyl)carbodiimide, the reaction solvent of step (1) is N,N-dimethylformamide, the reaction solvent of step (2) is one or a combination of N,N-dimethylformamide and dimethyl sulfoxide.

The compound of formula VII involved in the above two preparation methods can be obtained commercially, e.g., commercially available from Alfa Aesar. The said compound of formula VII can also be prepared as follows: an appropriate amount of di-$C_{1-6}$ alkoxy-carbonyl compound is dissolved in acetic anhydride, heated and refluxed for 4 hours, after concentrating the reaction liquid, an appropriate amount of xylene is added to the concentrate, then the mixture is concentrated and dried to obtain the compound of formula VII.

The present invention also provides a pharmaceutical composition which comprises a pharmaceutically effective amount of gemcitabine derivatives of formula I and a pharmaceutically acceptable excipient or additive. The pharmaceutical composition may be in the customary formulation.

The present invention also provides the application of compound of formula I in the preparation of anti-tumor drugs.

In one embodiment, the said tumor is drug-resistant tumor. The term "tumor drug-resistance" refers to: direct or indirect use of antitumor drugs for therapy is ineffective, or previously effective drug is ineffective when applied on treatment of tumor recurrence or metastasis.

Specifically, the formula I compounds of the present invention is mainly used for the preparation of drugs on the treatment of tumor drug-resistance, which is due to that the tumor cell is resistant to cytotoxic drugs, targeted small molecule drugs, macromolecular antibody drugs and immunomodulatory antitumor drugs.

Furthermore, the present invention also provides an application of gemcitabine derivatives of formula I in the preparation of anti-tumor drugs as prodrugs. Thus, the gemcitabine derivatives provided in the present invention can be applied as prodrugs on gemcitabine-adaptive tumor treatment by oral administration.

The present invention also provides a method of treating tumor, comprising administering the formula (I) compound of the present invention to a subject in need.

In one embodiment, the said tumor is drug-resistant tumor.

The present invention further provides a method on the treatment of tumor drug-resistance, which is due to that the tumor cell is resistant to cytotoxic drugs, targeted small molecule drugs, macromolecular antibody drugs and immunomodulatory antitumor drugs, comprising administering the formula (I) compound of the present invention to a subject in need.

The present invention has used gemcitabine as a precursor compound to obtain a series of novel compounds by modifying its structure, and found that most of the compounds have significant anti-tumor activity by activity screening, moreover, their inhibitory activity to drug-resistant tumor cell is far superior to gemcitabine, and also their toxicity is very low, therefore the result is amazing.

In summary, the structural design of compounds in the present invention is rational, optimized and filtered compounds have double-target mechanism of CDK inhibition and DNA synthesis inhibition, the preparation starting materials have extensive sources and are easily obtained, the preparation method is simple and easy to operate, the reaction condition is mild, moreover, the yield of the product is high, so that industrial production on a large scale is facilitated.

DETAILED DESCRIPTION OF THE EMBODIMENTS

Next, further description will be present in combination with specific embodiments, but the scope of the present invention is not limited by the following examples. There is one thing should be noted that the examples described below are not to be construed as limiting the scope of the present invention, any improvements made based on the present invention is not contrary to the spirit of the present invention.

Preparation example: Preparation of the compound of formula VII (e.g. heptanoic anhydride)

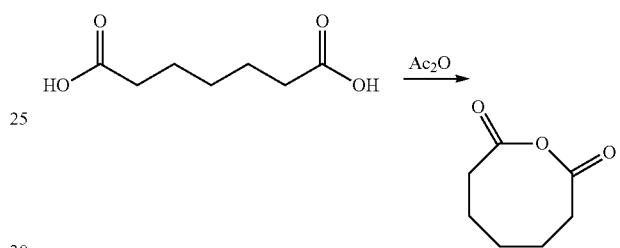

3.2 g heptane diacid was dissolved in 65 mL acetic anhydride, heated and refluxed for 4 hours, then the reaction liquid was concentrated. 20 mL xylene was added to the concentrate, then the mixture was concentrated and dried to obtain pink solid quantitively.

In the present invention, the compounds of number GI-01 to GI-03 can be synthesized by the following reaction scheme:

Step 1:

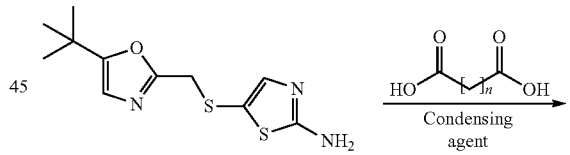

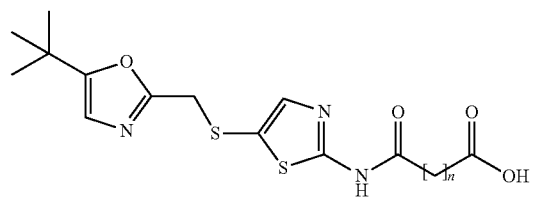

Step 2:

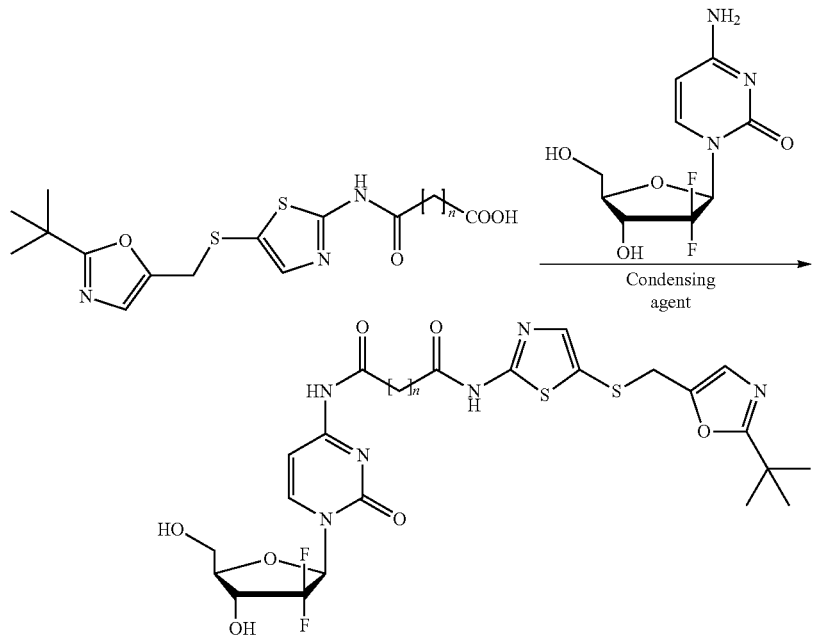

Wherein, n is 0 or 1 or 2

Example 1: Preparation of Compound No. GI-01

Step 1: 5-(((5-tert-butyl)oxazol-2-yl)methyl)thio)thiazol-2-amine (1.35 g, 9.5 mmol, 1.1 equivalent), oxalic acid (0.774 g, 8.6 mmol, 1 equivalent), 1-hydroxybenzotriazole monohydrate (1.46 g, 9.5 mmol), N-methylmorpholine (0.961 g, 9.5 mmol) were dissolved in 15 mL N,N-dimethylformamide, then 1-(3-dimethylamino propyl)-3-ethylcarbodiimide hydrochloride (2.154 g, 11.2 mmol, 1.3 equivalent) was added, protected by nitrogen, and stirred for 2 hours at room temperature. Then 40 mL saturated brine was added to the reaction solution to quench the reaction, extracted by dichloromethane (50 mL×5), organic layer was combined, dried over anhydrous sodium sulfate, concentrated, then purified by silica gel column chromatography (petroleum ether:ethyl acetate=10:1 to 2:1) to obtain 1.41 g white solid, 7-((5-(((2-t-butyl)oxazol-5-yl)methyl)thio)thiazol-2-yl)amino-7-oxo-acetic acid, in a yield of 82%.

$^1$H NMR (CDCl$_3$, 300 MHz): 7.27 (s, 1H), 6.61 (s, 1H), 3.89 (s, 2H), 1.26 (s, 9H). HRMS (ESI) [C$_{13}$H$_{15}$N$_3$O$_4$S$_2$—H]$^+$ calculated value: 342.4133, found value: 342.4129.

Step 2: 7-((5-(((2-t-butyl)oxazol-5-yl)methyl)thio)thiazol-2-yl)amino-7-oxo-acetic acid (1.50 g, 4.4 mmol, 1 equivalent), gemcitabine (1.32 g, 4.4 mmol, 1 equivalent), 1-hydroxybenzotriazole monohydrate (0.674 g, 4.4 mmol), N-methylmorpholine (0.445 g, 4.4 mmol) were dissolved in 6 mL N,N-dimethylformamide/dimethylsulfoxide (3:1) mixed solvent, 1-(3-dimethylamino propyl)-3-ethylcarbodiimide hydrochloride (1.096 g, 5.7 mmol, 1.3 equivalent) was added, protected by argon, heated to 55° C., stirred for 19 hours. Then 20 mL saturated brine was added to the reaction solution to quench the reaction, extracted by dichloromethane (50 mL×5), organic layer was combined, washed sequentially with saturated sodium carbonate solution, water, saturated brine, dried over anhydrous sodium sulfate, concentrated, then purified by silica gel column chromatography(dichloromethane:methanol=50:1 to 10:1) to obtain 712 mg compound GI-01, white solid, in a yield of 27%.

$^1$H NMR (DMSO-d6, 300 MHz): 12.29 (s, 1H), 10.88 (s, 1H), 8.23 (d, J=7.6 Hz, 1H), 7.34 (s, 1H), 7.26 (d, J=7.6 Hz, 1H), 6.70 (s, 1H), 6.31 (d, J=6.4 Hz, 1H), 6.19 (t, J=7.3, 1H), 5.31 (t, J=5.2, 1H), 4.18 (m, 1H), 4.09 (s, 2H), 3.91 (d, J=8.2, 1H), 3.82 (d, br, 1H), 3.65 (m, 1H), 1.33 (s, 9H). HRMS (ESI) [C$_{22}$H$_{24}$F$_2$N$_6$O$_7$S$_2$—H]$^+$ calculated value: 587.5962, found value: 587.5960.

Example 2: Preparation of Compound No. GI-02

The title compound was prepared according to example 1, but malonic acid was used as starting material to replace oxalic acid in step 1, and monitored by TLC to the end of the reaction, a pale yellow solid was obtain as compound No. GI-02.

$^1$H NMR (DMSO-d6, 300 MHz): 12.24 (s, 1H), 10.93 (s, 1H), 8.25 (d, J=7.6 Hz, 1H), 7.36 (s, 1H), 7.23 (d, J=7.6 Hz, 1H), 6.77 (s, 1H), 6.33 (d, J=6.4 Hz, 1H), 6.16 (t, J=7.3, 1H), 5.31 (t, J=5.2, 1H), 4.13 (m, 1H), 4.02 (s, 2H), 3.91 (d, J=8.2, 1H), 3.84 (d, br, 1H), 3.66 (m, 1H), 1.28 (s, 2H), 1.34 (s, 9H). HRMS (ESI) [C$_{23}$H$_{26}$F$_2$N$_6$O$_7$S$_2$—H]$^+$ calculated value: 601.6227, found value: 601.6230.

Example 3: Preparation of Compound No. GI-03

The title compound was prepared according to example 1, but succinic acid was used as starting material to replace oxalic acid in step 1, and monitored by TLC to the end of the reaction, a pale yellow solid was obtain as the compound No. GI-03.

$^1$H NMR (DMSO-d6, 300 MHz): 12.25 (s, 1H), 10.91 (s, 1H), 8.22 (d, J=7.6 Hz, 1H), 7.33 (s, 1H), 7.21 (d, J=7.6 Hz, 1H), 6.79 (s, 1H), 6.32 (d, J=6.4 Hz, 1H), 6.15 (t, J=7.3, 1H), 5.38 (t, J=5.2, 1H), 4.12 (m, 1H), 4.12 (s, 2H), 3.81 (d, J=8.2, 1H), 3.85 (d, br, 1H), 3.69 (m, 1H), 1.28 (m, 4H), 1.34 (s,

9H). HRMS (ESI) [C$_{24}$H$_{28}$F$_2$N$_6$O$_7$S$_2$—H]$^+$ calculated value: 615.6493, found value: 615.6499.

In the present invention, the compounds of number GI-04 and GI-05 can be synthesized by the following reaction scheme:

Step 1:

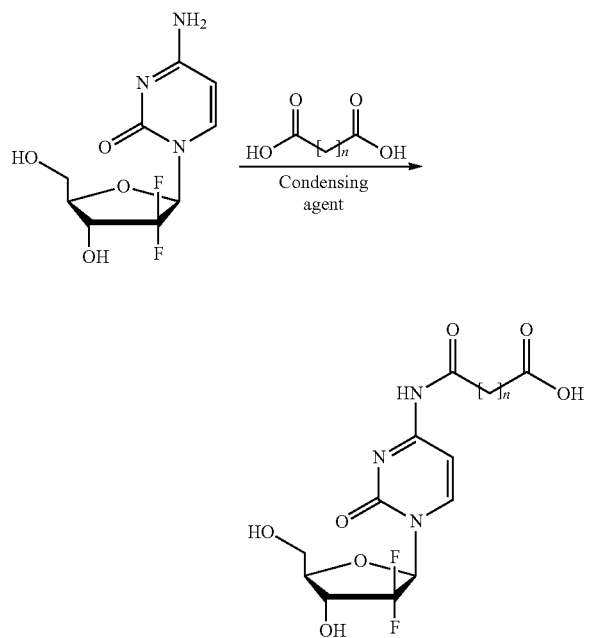

Step 2:

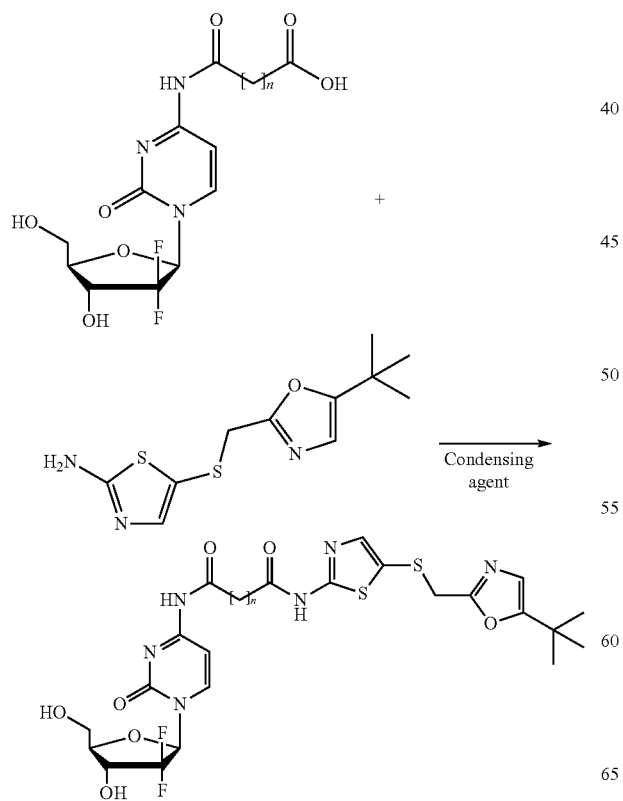

Wherein, n is 3 or 4

Example 4: Preparation of Compound No. GI-04

Step 1: Glutaric acid (0.32 g, 2.42 mmol, 1.1 Equivalent), gemcitabine (0.66 g, 2.2 mmol, 1 equivalent), 1-hydroxybenzotriazole monohydrate (0.337 g, 2.2 mmol), N-methylmorpholine (0.223 g, 2.2 mmol) were dissolved in 4 mL N,N-dimethylformamide, 1-(3-dimethylamino propyl)-3-ethylcarbodiimide hydrochloride (0.548 g, 2.8 mmol, 1.3 equivalent) was added, protected by nitrogen, stirred at room temperature for 3 hours. Then 20 mL saturated brine was added to the reaction solution to quench the reaction, extracted by dichloromethane (10 mL×5), organic layer was combined, dried over anhydrous sodium sulfate, concentrated, then purified by silica gel column chromatography (petroleum ether:ethyl acetate=10:1 to 2:1) to obtain 0.89 g white solid, 5-((1-((2R,4R,5R)-3,3-difluoro-4-hydroxy-5-(hydroxymethyl) tetrahydrofuran-2-yl)-2-oxo-1,2-dihydropyrimidin-4-yl)amino)-5-oxo-pentanoic acid, in a yield of 94%.

HRMS (ESI) [C$_{14}$H$_{17}$F$_2$N$_3$O$_7$—H]$^+$ calculated value: 378.3049, found value: 378.3055.

Step 2: 5-((1-((2R,4R,5R)-3,3-difluoro-4-hydroxy-5-(hydroxymethyl) tetrahydrofuran-2-yl)-2-oxo-1,2-dihydro-pyrimidin-4-yl)amino)-5-oxo-pentanoic acid (1.51 g, 4 mmol, 1.0 equivalent), 5-(((5-tert-butyl) oxazol-2-yl) methyl) thio) thiazol-2-amine (1.08 g, 4 mmol, 1.0 equivalent), 1-hydroxybenzotriazole monohydrate (0.613 g, 4.0 mmol), N-methylmorpholine (0.404 g, 4.0 mmol) were dissolved in 6 mL N,N-dimethylformamide/dimethylsulfoxide (3:1) mixed solvent, 1-(3-dimethylamino propyl)-3-ethylcarbodiimide hydrochloride (1.00 g, 5.2 mmol, 1.3 equivalent) was added, protected by argon, heated to 55° C., stirred for 16 hours. Then 20 mL saturated brine was added to the reaction solution to quench the reaction, extracted by dichloromethane (50 mL×5), organic layer was combined, washed sequentially with saturated sodium carbonate solution, water, saturated brine, dried over anhydrous sodium sulfate, concentrated, then purified by silica gel column chromatography(dichloromethane:methanol=50:1 to 10:1) to obtain 811 mg the title compound, white solid, in a yield of 32%.

HRMS (ESI) [C$_{25}$H$_{30}$F$_2$N$_6$O$_7$S$_2$—H]$^+$ calculated value: 629.6759, found value 629.6762.

Example 5: Preparation of Compound No. GI-05

The title compound was prepared according to example 4, but adipic acid was used as starting material to replace glutaric acid in step 1, and monitored by TLC to the end of the reaction, a pale yellow solid was obtain as compound No. GI-05.

HRMS (ESI) [C$_{26}$H$_{32}$F$_2$N$_6$O$_7$S$_2$—H]$^+$ calculated value: 643.7025, found value: 643.7030.

In the present invention, the compounds of number GI-06 to GI-07 can be synthesized by the following reaction scheme:

Step 1:

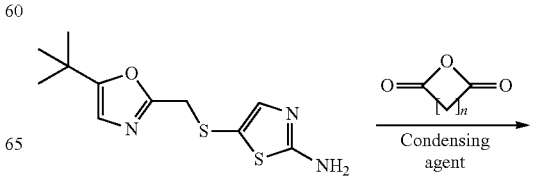

-continued

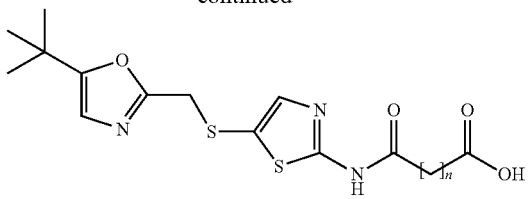

Step 2:

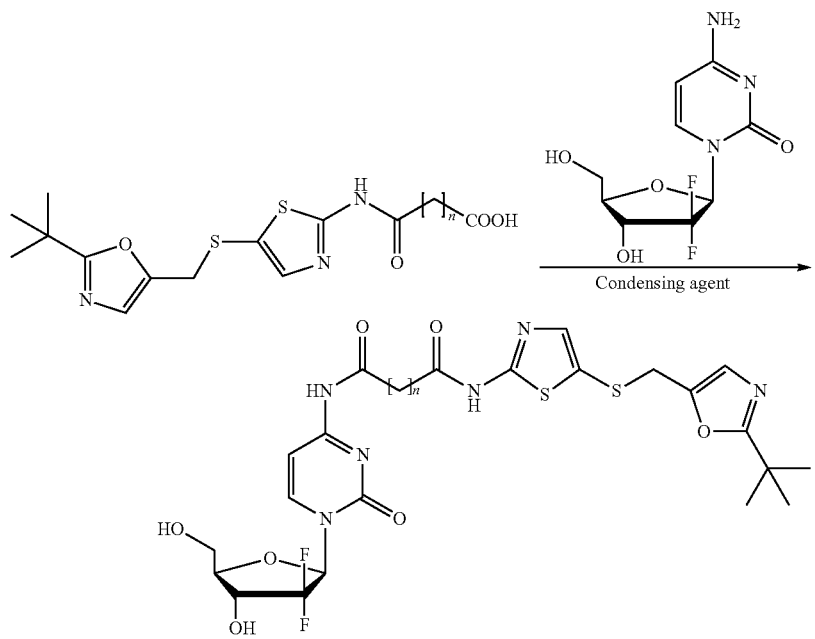

Wherein, n is 5 or 6

Example 6: Preparation of Compound No. GI-06

Step 1: Pimelic anhydride (2.33 g, 8.6 mmol, 1 equivalent) and 5-(((5-tert-butyl) oxazol-2-yl) methyl) thio) thiazol-2-amine (1.35 g, 9.5 mmol, 1.1 equivalent) were dissolved in 15 mL N,N-dimethylformamide, heated to 100° C., 16 hours later, 30 mL water was added to the reaction solution to quench the reaction, extracted by ethyl acetate (50 mL×4), organic layer was combined, washed by saturated brine, dried over anhydrous sodium sulfate, concentrated, then purified by silica gel column chromatography (petroleum ether:ethyl acetate=10:1 to 2:1) to obtain 1.8 g pale yellow solid, 7-((5-(((2-t-butyl)oxazol-5-yl)methyl)thio)thiazol-2-yl)amino-7-oxo-heptanoic acid, in a yield of 51%.

$^1$H NMR (CDCl$_3$, 300 MHz): 7.25 (s, 1H), 6.60 (s, 1H), 3.96 (s, 2H), 2.50 (quintet, J=7.2 Hz, 2H), 2.38 (t, J=7.2 Hz, 1H), 2.09 (s, 2H), 1.79 (quintet, J=7.1 Hz, 2H), 1.69 (quintet, J=8.1 Hz, 1H), 1.46 (quintet, J=7.0 Hz, 2H), 1.26 (s, 9H). HRMS (ESI) [C$_{18}$H$_{25}$N$_3$O$_4$S$_2$—H]$^-$ calculated value: 410.1214, found value: 410.1219.

Step 2: 7-((5-(((2-t-butyl)oxazol-5-yl)methyl)thio)thiazol-2-yl)amino-7-oxo-heptanoic acid (1.815 g, 4.4 mmol, 1 equivalent), gemcitabine (1.32 g, 4.4 mmol, 1 equivalent), 1-hydroxybenzotriazole monohydrate (0.674 g, 4.4 mmol), N-methylmorpholine (0.445 g, 4.4 mmol) were dissolved in 6 mL N,N-dimethylformamide/dimethylsulfoxide (3:1) mixed solvent, 1-(3-dimethylamino propyl)-3-ethylcarbodiimide hydrochloride (1.096 g, 5.7 mmol, 1.3 equivalent) was added, protected by argon, heated to 55° C., stirred for 19 hours. Then 20 mL saturated brine was added to the reaction solution to quench the reaction, extracted by dichloromethane (50 mL×5), organic layer was combined, washed sequentially with saturated sodium carbonate solution, water, saturated brine, dried over anhydrous sodium sulfate, concentrated, then purified by silica gel column chromatography(dichloromethane:methanol=50:1 to 10:1) to obtain 608 mg the title compound, white solid, in a yield of 21%.

$^1$H NMR (DMSO-d6, 300 MHz): 12.20 (s, 1H), 10.98 (s, 1H), 8.25 (d, J=7.6 Hz, 1H), 7.38 (s, 1H), 7.29 (d, J=7.6 Hz, 1H), 6.71 (s, 1H), 6.32 (d, J=6.4 Hz, 1H), 6.18 (t, J=7.3, 1H), 5.30 (t, J=5.2, 1H), 4.17 (m, 1H), 4.06 (s, 2H), 3.90 (d, J=8.2, 1H), 3.82 (d, br, 1H), 3.66 (m, 1H), 2.42 (t, J=7.1 Hz, 4H), 1.58 (m, 4H), 1.28 (m, 2H), 1.3 (s, 9H). $^{13}$C NMR (DMSO-d6, 75 MHz): 174.42, 171.98, 163.33, 161.67, 161.32, 159.17, 154.68, 145.48, 145.16, 123.45, 120.51, 118.97, 96.40, 81.54, 69.17, 68.89, 68.56, 59.27, 36.69, 35.06, 34.44, 31.36, 28.74, 28.36, 24.84, 24.48. LC-MS (Q-TOF, 100 μm/mL) m/z [M+H$^+$] found value: 657.19635.

Example 7: Preparation of Compound No. GI-07

The title compound was prepared according to example 6, but suberic acid was used as starting material to replace pimelic acid in step 1, and monitored by TLC to the end of the reaction, a white solid was obtained as compound No. GI-07.

HRMS (ESI) [C$_{28}$H$_{36}$F$_2$N$_6$O$_7$S$_2$—H]$^+$ calculated value: 671.7556, found value: 671.7560.

In the present invention, the compounds of GI-08 and GI-09 can be synthesized by the following reaction scheme:

Step 1:

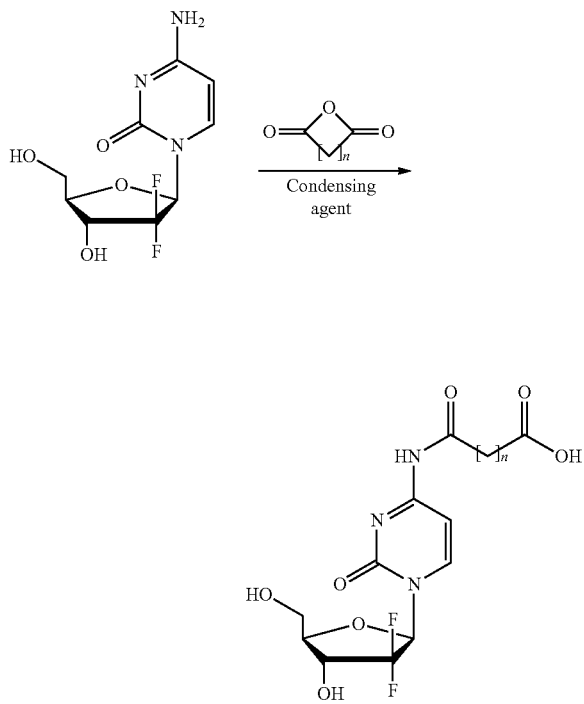

Step 2:

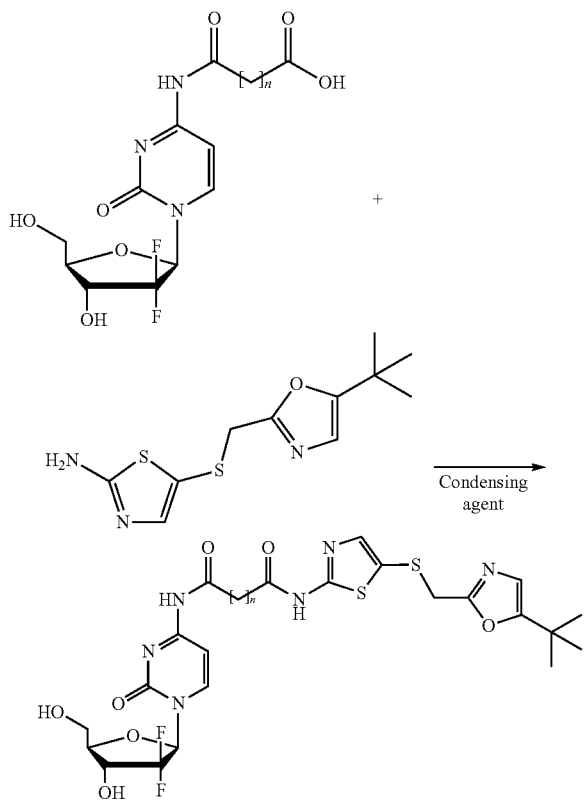

Wherein, n is 7 or 8.

Example 8: Preparation of Compound No. GI-08

Step 1: Azelaic anhydride (0.376 g, 2.0 mmol, 1 equivalent), gemcitabine (0.66 g, 2.2 mmol, 1.1 equivalent) were dissolved in 15 mL N,N-dimethylformamide, heated to 100° C., 19 hours later, 30 mL water was added to the reaction solution to quench the reaction, extracted by ethyl acetate (50 mL×4), organic layer was combined, washed by saturated brine, dried over anhydrous sodium sulfate, concentrated, then purified by silica gel column chromatography (petroleum ether:ethyl acetate=10:1~2:1) to obtain 796 mg pale yellow solid, 5-((1-((2R,4R,5R)-3,3-difluoro-4-hydroxy-5-(hydroxymethyl) tetrahydrofuran-2-yl)-2-oxo-1,2-dihydro-pyrimidin-4-yl)amino)-5-oxo-nonanoic acid, in a yield of 91%.

HRMS (ESI) $[C_{18}H_{25}F_2N_3O_7—H]^+$ calculated value: 434.4112, found value: 434.4120.

Step 2: The same preparation method as step 2 in example 4, 5-((1-((2R,4R,5R)-3,3-difluoro-4-hydroxy-5-(hydroxymethyl) tetrahydrofuran-2-yl)-2-oxo-1,2-dihydro-pyrimidin-4-yl)amino)-5-oxo-nonanoic acid was used as starting material to replace 5-((1-((2R,4R,5R)-3,3-difluoro-4-hydroxy-5-(hydroxymethyl)tetrahydrofuran-2-yl)-2-oxo-1,2-dihydro-pyrimidin-4-yl)amino)-5-oxo-pentanoic acid, and monitored by TLC to the end of the reaction, a white solid was obtain as compound GI-08.

HRMS (ESI) $[C_{29}H_{38}F_2N_6O_7S_2—H]^+$ calculated value: 685.7822, found value: 685.7830.

Example 9: Preparation of Compound No. GI-09

The same preparation method as example 8, except sebacic acid was used as starting material to replace azelaic acid in step 1, and monitored by TLC to the end of the reaction, a pale yellow solid was obtained as compound No. GI-09.

HRMS (ESI) $[C_{30}H_{40}F_2N_6O_7S_2—H]^+$ calculated value: 699.8088, found value: 699.8090.

Example 10: Test of the Cytotoxic Activities of Gemcitabine and its Derivatives Against Drug-Resistant Tumor Cell Lines Purpose: Compare differences of cytotoxic activity against drug-resistant tumor cell lines between gemcitabine derivatives (Compounds of examples 1-9 of the present invention) and gemcitabine (known compound, as "comparative example" in the table below).

Materials and Methods: Human breast cancer doxorubicin-resistant cell line MCF-7-ADR was cultured in 1640 medium containing 5% fetal calf serum; gemcitabine and its derivative GI-06 were dissolved in DMSO, frozen preserved at −20° C., and diluted by 1640 medium containing 5% fetal calf serum to the appropriate concentration before they were used. The final concentration of DMSO solution was 0.5%. Activity tests: MCF-7-ADR cells in the logarithmic growth phase were seeded $3\times10^3$ per well in 96-well culture plates. The medium was changed after incubating for 24 hours by adding test solutions at different concentrations, while the control group was added DMSO medium with concentration of 0.5%, and the cells continued to be incubated for 48 hours. Then the cell activity was assayed by MTT. Inhibition rate (%)=(1-(absorbance of the blank control group−absorbance of the administration group)/absorbance of the blank control group)×100%; IC50: calculated by Bliss method.

Experimental results: Table 1

TABLE 1

Effect of gemcitabine and its derivatives on the activities of drug-resistant tumor cells

| comparative example | Name | MCF-7-ADR(IC$_{50}$ μM) |
|---|---|---|
| | gemcitabine | >10 |
| Example 1 | GI-01 | 5.56 |
| Example 2 | GI-02 | 4.77 |
| Example 3 | GI-03 | 6.13 |
| Example 4 | GI-04 | 3.15 |
| Example 5 | GI-05 | 2.46 |
| Example 6 | GI-06 | 1.38 |
| Example 7 | GI-07 | 3.55 |
| Example 8 | GI-08 | 3.29 |
| Example 9 | GI-09 | 2.66 |

From Table 1, the inhibitory activity of number GI-01 to GI-09 gemcitabine derivatives provided by the present invention against human breast cancer drug-resistant cell line MCF-7-ADR proliferation was significantly enhanced with respect to gemcitabine; especially compound GI-06 has the strongest anti-tumor activity.

Example 11: Experimental Study of the Compounds' Influence to the Growth of Subcutaneous Transplanted Tumor in Nude Mice Bearing HCT-116 Colon Cancer Purpose: 4 compounds' influence to the growth of subcutaneous transplanted tumor in nude mice bearing HCT-116 colon cancer
Materials and Methods:
Test sample: GI-04, GI-05, GI-06, GI-09,
Positive control: Gemcitabine hydrochloride.
Experimental animals: Nude mice, female, 4-5 weeks old, 60 cases.
Cell lines: HCT-116 colon cancer cell.
Modeling: Five mice were inoculated by cell suspension before the experiment, after passaging 4 times in nude mice, prepared model by subcutaneous inoculation using the interpolation block tumor masses.

Grouping: When tumor volume grew to about 100 mm$^3$, nude mice which reached the standard were randomly divided into six groups, namely solvent control group, gemcitabine hydrochloride group, GI-04 group, GI-05 group, GI-06 group, GI-09 group.

Dosage of administration: Gemcitabine hydrochloride for the control group was adminstered at 160 mg/kg, GI-04 group, GI-05 group, GI-09 group were adminstered at 15 mg/kg, GI-06 high dosage group was adminstered at 15 mg/kg, GI-06 medium dosage group was adminstered at 10 mg/kg, GI-06 low dosage group was adminstered at 5 mg/kg, "solvent control" group was adminstered the corresponding solvent of GI-06 (0.1% Tween-80 and 0.9% hydroxypropyl methyl cellulose solution).

Route of administration: Gemcitabine hydrochloride group was adminstered by intraperitoneal injection, the rest groups were adminstered by oral gavage.
The adminstered volume: 0.1 ml/10 g
Frequency of adminstered: Gemcitabine hydrochloride was administered twice in the first week (D1 and D4), twice in total; GI-04, GI-05, GI-09 groups were administered five consecutive days in a week, two days pause, 10 times in total; GI-06 high dosage group was administered five consecutive days in a week, two days pause, 10 times in total. GI-06 medium dosage group was administered 7 days in the first week, 5 days in the second week due to the animal's condition, 12 times in total. Frequency of GI-06 low dosage group was the same with GI-06 medium dosage group.

Observation time: Consecutive observation for 15 days after administration, tumor volume was measured twice a week. Stop administration at the 15th day.
Statistical Methods: Excel statistical software package, ANOVA analysis.
Experimental results: Table 2

TABLE 2

Experimental study of the compounds' influence to the growth of transplantated tumor in nude mice bearing HCT-116 colon cancer

| Group | Animal number D1 | Animal number D15 | Weight (g) D1 | Weight (g) D15 | Tumor volume (mm$^3$) D1 | Tumor volume (mm$^3$) D15 | T/C (%) D15 | Time to death |
|---|---|---|---|---|---|---|---|---|
| Solvent control | 6 | 6 | 19.5 ± 1.1 | 18.7 ± 1.0 | 95.08 ± 16.21 | 1664.30 ± 355.06 | / | / |
| Gemcitabine hydrochloride | 5 | 5 | 19.5 ± 0.8 | 20.0 ± 1.5 | 97.89 ± 10.39 | 99.90 ± 55.92☆ | 5.83 | / |
| GI-06 low dosage group | 5 | 5 | 19.4 ± 1.0 | 17.2 ± 0.8* | 93.82 ± 30.42 | 45.172 ± 214.92☆ | 27.50 | / |
| GI-06 medium dosage group | 5 | 5 | 18.9 ± 0.7 | 17.5 ± 1.1 | 97.09 ± 15.71 | 222.43 ± 113.48☆ | 13.09 | / |
| GI-06 high dosage group | 6 | 4 | 19.4 ± 0.6 | 18.0 ± 1.5 | 94.08 ± 11.32 | 208.14 ± 80.53☆ | 12.64 | D7, D8 |
| GI-04 | 5 | 5 | 19.2 ± 1.0 | 19.9 ± 1.2 | 94.55 ± 22.52 | 1008.78 ± 174.29 | 60.9 | / |
| GI-05 | 5 | 4 | 18.9 ± 0.9 | 18.1 ± 1.2 | 95.18 ± 17.56 | 935.14 ± 130.33 | 56.14 | D8 |
| GI-09 | 5 | 5 | 19.3 ± 1.1 | 18.6 ± 1.4 | 95.69 ± 25.47 | 724.50 ± 158.19 | 43.26 | / |

Note:
*p < 0.05,
☆p < 0.01.

Experimental results showed that in the 4 compounds, GI-06 at 5 mg/kg, 10 mg/kg, 15 mg/kg showed significant inhibition effect on the growth of transplantation tumors in nude mice bearing HCT-116 colon cancer, T/C was 27%, 13% and 12%, respectively. While the control group which was adminstered gemcitabine hydrochloride by intraperitoneal injection at 160 mg/kg showed inhibition effect on the growth of tumor after twice administration, T/C was 5.8%.

The experimental results showed that even the low dosage group which was adminstered at 5 mg/kg could achieve good inhibition effect on the growth of tumor by successive administration, which suggested to reduce dosage in the next batch so that to get the lowest effective dosage.

Example 12: Experimental Study of the Compound GI-06' Influence to Subcutaneous Transplanted Tumor Growth in Nude Mice Bearing A2780 Ovarian Cancer Purpose: The compound GI-06' influence to subcutaneous transplanted tumor growth in nude mice bearing A2780 ovarian cancer.

Materials and Method:

Test sample: GI-06; Positive control: gemcitabine hydrochloride

Experimental animals: nude mice, female, 4-5 weeks old, 40 cases.

Cell lines: A2780 ovarian cancer cell, purchased from Shanghai institute of cell biology.

Modeling: Five mice were inoculated by cell suspension before the experiment, after passaging 2 times in nude mice, prepared model by subcutaneous inoculation using the interpolation block tumor masses.

Grouping: When tumor volume grew to 100 mm$^3$, nude mice which reached standard were randomly divided into five groups, namely solvent control group, gemcitabine hydrochloride group, GI-06 high, medium, low dosage groups, 6 nude mice in each group.

Dosage of administration: Gemcitabine hydrochloride for control group was adminstered at 160 mg/kg, GI-06 high dosage group was adminstered at 12 mg/kg, GI-06 medium dosage group was adminstered at 8 mg/kg, GI-06 low dosage group was adminstered at 4 mg/kg, "solvent control" group was adminstered the corresponding solvent of GI-06 (0.1% Tween-80 and 0.9% hydroxypropyl methyl cellulose solution).

Route of administration: Gemcitabine hydrochloride group was adminstered by intraperitoneal injection, the rest groups were adminstered by oral gavage.

The administration volume: 0.1 ml/10 g

Frequency of administration: Gemcitabine hydrochloride was respectively adminstered twice in the first and third week (D1, D4, D15, D18), 4 times in total; Each GI-06 dosage group was adminstered once a day, 21 days in total.

Observation time: Consecutive observation for 21 days after administration, tumor volume was measured twice a week. Animals were sacrificed on the 22nd day, the tumors were weighed.

Statistical Methods: Excel statistical software package, ANOVA analysis.

Experimental results: Table 4

TABLE 4

Experimental study of the compound GI-06' influence to transplantated tumor growth in nude mice bearing A2780 ovarian cancer

| Group | animal number D 1 | animal number D22 | Weight (g) D 1 | Weight (g) D22 | Tumor volume (mm$^3$) D 1 | Tumor volume (mm$^3$) D22 | T/C (%) D22 | Time to death |
|---|---|---|---|---|---|---|---|---|
| Solvent control | 6 | 6 | 19.5 ± 0.7 | 25.9 ± 2.3 | 121.07 ± 54.05 | 4535.67 ± 1745.47 | / | / |
| Gemcitabine hydrochloride | 6 | 4 | 20.3 ± 1.1 | 22.2 ± 0.9 | 121.24 ± 36.57 | 59.97 ± 72.33☆ | 1.32 | D5, D8 |
| GI-06 low dosage group (4 mg/kg) | 6 | 6 | 19.9 ± 0.7 | 23.9 ± 1.6 | 118.63 ± 70.63 | 1757.57 ± 1306.74☆ | 39.55 | / |
| GI-06 medium dosage group (8 mg/kg) | 6 | 6 | 19.3 ± 1.0 | 21.1 ± 0.9 | 117.15 ± 42.40 | 92.38 ± 159.91☆ | 2.11 | / |
| GI-06 high dosage group (12 mg/kg) | 6 | 6 | 19.1 ± 0.7 | 20.9 ± 1.1 | 114.83 ± 27.91 | 19.83 ± 35.11☆ | 0.46 | / |

Note:
☆p < 0.01.

The model used in the experiment was model of transplanted tumor of nude mice bearing A2780 ovarian cancer. The experimental results showed that, GI-06 at 4 mg/kg, 8 mg/kg, and 12 mg/kg showed significant inhibition effect on A2780 tumor growth in a dosage-dependent manner, T/C was 39.55%, 2.11% and 0.46%, respectively. While in the control group wherein gemcitabine was injected intraperitoneally, the T/C was 1.32%. No obvious toxicity appeared in the three groups which were administered continuously in this experiment, and there was no effect on body weight of animals.

The invention claimed is:
1. A compound of formula I:

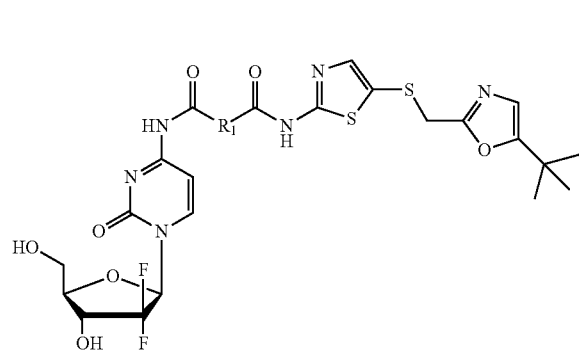

wherein
R₁ is selected from unsubstituted or substituted $C_{1-10}$ alkyl, unsubstituted or substituted $C_{2-10}$ alkenyl, unsubstituted or substituted $C_{2-10}$ alkynyl, unsubstituted or substituted $C_{3-7}$ cycloalkyl, unsubstituted or substituted $C_{3-7}$ cycloalkyloxy, wherein the said substituent is selected from one or more of halogen, cyano, nitro, amino, trifluoromethyl, thiol, hydroxyl, carboxyl, carbonyl, $C_{1-6}$ alkyl, $C_{2-6}$ alkenyl, $C_{2-6}$ alkynyl, $C_{1-6}$ alkoxy, $C_{1-6}$ alkoxycarbonyl and —NH—;

or R₁ is optionally substituted aryl, wherein the said substituent is selected from one or more of hydrogen, hydroxyl, carboxyl, nitro, halogen, $C_{1-6}$ alkyl and $C_{1-6}$ alkoxy.

2. The compound according to claim 1, wherein said optionally substituted aryl is phenyl, benzyl or naphthyl.

3. The compound according to claim 1, wherein R₁ is selected from unsubstituted or substituted $C_{3-10}$ alkyl, unsubstituted or substituted $C_{3-10}$ alkenyl, unsubstituted or substituted $C_{3-10}$ alkynyl, unsubstituted or substituted $C_{3-7}$ cycloalkyl, and unsubstituted or substituted $C_{3-7}$ cycloalkyloxy.

4. The compound according to claim 1, wherein said halogen is F, Cl, Br or I.

5. The compound according to claim 1, wherein R₁ is selected from unsubstituted or substituted $C_{4-9}$ alkyl, unsubstituted or substituted $C_{4-9}$ alkenyl, unsubstituted or substituted $C_{4-9}$ alkynyl, unsubstituted or substituted $C_{3-7}$ cycloalkyl, and unsubstituted or substituted $C_{3-7}$ cycloalkyloxy, wherein the substituent is selected from F and Cl.

6. A pharmaceutical composition comprising pharmaceutically effective amount of the compound according to claim 1 and a pharmaceutically acceptable excipient or additive.

7. A method of treating tumor, comprising administering an effective amount of the compound according to claim 1 to a subject in need thereof.

8. The method of claim 7, wherein said tumor is drug-resistant tumor.

9. A method of treating drug-resistant tumor, comprising administering an effective amount of the compound according to claim 1 to a subject in need thereof, wherein said tumor is resistant to cytotoxic drugs, targeted small molecule drugs, macromolecular antibody drugs and/or immunomodulatory antitumor drugs.

10. A method for preparing the compound according to claim 1, comprising:
(1) in the presence of a condensing agent, mixing a compound of formula IV

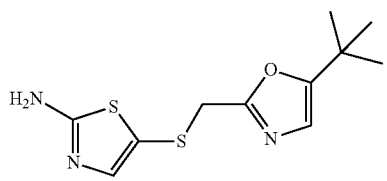

with a compound of formula V or formula VII,

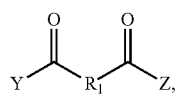

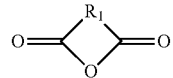

obtaining an intermediate of formula III via amidation reaction,

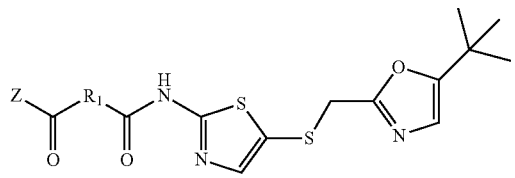

wherein the definition of R₁ is the same as claim 1, and wherein Y and Z are each independently selected from OH, F, Cl, Br or with the proviso that when the compound of formula IV reacts with the compound of formula VII, Z in the compound of formula III is OH; and (2) in the presence of a condensing agent, mixing the intermediate of formula III obtained in step (1) with a compound of formula II,

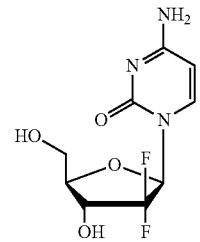

thereby obtaining the compound according to claim 1 via amidation reaction.

11. The method of claim 10, wherein said steps (1) and (2) are conducted at 0° C. to 150° C.

12. The method of claim 11, wherein said steps (1) and (2) are conducted at 20° C. to 120° C.

13. The method of claim 10, wherein said condensing agent is one or more of 1-hydroxybenzotriazole, 1-hydroxy-7-azo-benzotriazole, 3-hydroxy-1,2,3-benzotriazine-4(3H)-one, 1-ethyl-(3-dimethylaminopropyl)carbodiimide, N,N-dicyclohexyl carbodiimide, and N,N-diisopropyl carbodiimide.

14. The method of claim 13, wherein said condensing agent is one or a combination of 1-hydroxybenzotriazole and 1-ethyl-(3-dimethylaminopropyl)carbodiimide, and wherein step (1) is conducted in N,N-dimethylformamide, and step (2) is conducted in a solvent selected from one or a combination of N,N-dimethylformamide and dimethyl sulfoxide.

15. The method of claim 10, wherein said step (1) and step (2) are conducted in a solvent selected from one or more of benzene, toluene, chloroform, n-hexane, cyclohexane, dichloromethane, 1,2-dichloroethane, methyl t-butyl ether, carbon tetrachloride, ethyl acetate, propyl acetate, butyl acetate, methanol, ethanol, acetone, tetrahydrofuran, diethyl ether, acetonitrile, N, N-dimethylformamide, and dimethyl sulfoxide.

16. A method for preparing the compound according to claim 1, comprising:
(1) in the presence of a condensing agent, mixing a compound of formula II

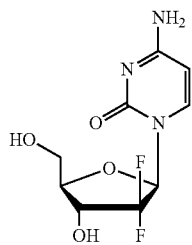

with a compound of formula V or formula VII,

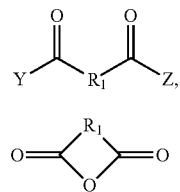

thereby obtaining an intermediate of formula VI via amidation reaction, wherein the definition of $R_1$ is the same as claim 1, and wherein Y and Z are each independently selected from OH, F, Cl, Br or I, with the proviso that, when the compound of formula II reacts with the compound of formula VII, Z in the compound of formula VI is OH, and

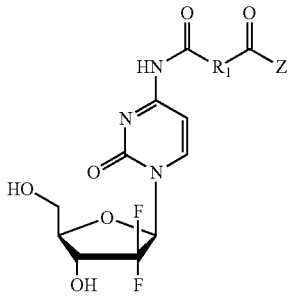

(2) in the presence of a condensing agent, mixing the intermediate of formula VI obtained in step (1) with a compound of formula IV,

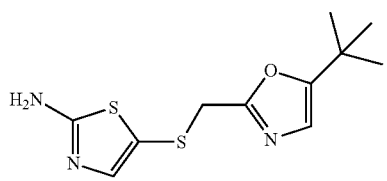

thereby obtaining the compound according to claim 1 via amidation reaction.

17. The method of claim 16, wherein said steps (1) and (2) are conducted at 0° C. to 150° C.

18. The method of claim 17, wherein said steps (1) and (2) are conducted at 20° C. to 120° C.

19. The method of claim 16, wherein said condensing agent is one or more of 1-hydroxybenzotriazole, 1-hydroxy-7-azo-benzotriazole, 3-hydroxy-1,2,3-benzotriazine-4(3H)-one, 1-ethyl-(3-dimethylaminopropyl)carbodiimide, N,N-dicyclohexyl carbodiimide, and N,N-diisopropyl carbodiimide.

20. The method of claim 16, wherein said step (1) and step (2) are conducted in the solvent selected from one or more of benzene, toluene, chloroform, n-hexane, cyclohexane, dichloromethane, 1,2-dichloroethane, methyl t-butyl ether, carbon tetrachloride, ethyl acetate, propyl acetate, butyl acetate, methanol, ethanol, acetone, tetrahydrofuran, diethyl ether, acetonitrile, N, N-dimethylformamide, and dimethyl sulfoxide.

21. The method of claim 19, wherein said condensing agent is one or a combination of 1-hydroxybenzotriazole and 1-ethyl-(3-dimethylaminopropyl)carbodiimide, and wherein step (1) is conducted in N,N-dimethylformamide, and step (2) is conducted in a solvent selected from one or a combination of N,N-dimethylformamide and dimethyl sulfoxide.

22. A compound selected from the group consisting of:

N-(5-(((5-(t-butyl) oxazol-2-yl)methyl)thio)thiazol-2-yl)-N'-(1-((2R,4R,5R)-3,3-difluoro-4-hydroxy-5-(hydroxymethyl)tetrahydrofuran-2-yl)-2-oxo-1,2-dihydropyrimidin-4-yl)oxamide, N-(5-(((5-(t-butyl) oxazol-2-yl)methyl)thio)thiazol-2-yl)-N'-(1-((2R,4R,5R)-3,3-difluoro-4-hydroxy-5-(hydroxymethyl)tetrahydrofuran-2-yl)-2-oxo-1,2-dihydropyrimidin-4-yl)malonamide, N-(5-(((5-(t-butyl) oxazol-2-yl)methyl)thio)thiazol-2-yl)-N'-(1-((2R,4R,5R)-3,3-difluoro-4-hydroxy-5-(hydroxymethyl)tetrahydrofuran-2-yl)-2-oxo-1,2-dihydropyrimidin-4-yl)succinamide, N-(5-(((5-(t-butyl) oxazol-2-yl)methyl)thio)thiazol-2-yl)-N'-(1-((2R,4R,5R)-3,3-difluoro-4-hydroxy-5-(hydroxymethyl)tetrahydrofuran-2-yl)-2-oxo-1,2-dihydropyrimidin-4-yl)glutaramide, N-(5-(((5-(t-butyl) oxazol-2-yl)methyl)thio)thiazol-2-yl)-N'-(1-((2R,4R,5R)-3,3-difluoro-4-hydroxy-5-(hydroxymethyl)tetrahydrofuran-2-yl)-2-oxo-1,2-dihydropyrimidin-4-yl)adipamide, N-(5-(((5-(t-butyl) oxazol-2-yl)methyl)thio)thiazol-2-yl)-N'-(1-((2R,4R,5R)-3,3-difluoro-4-hydroxy-5-(hydroxymethyl)tetrahydrofuran-2-yl)-2-oxo-1,2-dihydropyrimidin-4-yl)pimelamide, N-(5-(((5-(t-butyl) oxazol-2-yl)methyl)thio)thiazol-2-yl)-N'-(1-((2R,4R,5R)-3,3-difluoro-4-hydroxy-5-(hydroxymethyl)tetrahydrofuran-2-yl)-2-oxo-1,2-dihydropyrimidin-4-yl)suberamide, N-(5-(((5-(t-butyl) oxazol-2-yl)methyl)thio)thiazol-2-yl)-N'-(1-((2R,4R,5R)-3,3-difluoro-4-hydroxy-5-(hydroxymethyl)tetrahydrofuran-2-yl)-2-oxo-1,2-dihydropyrimidin-4-yl)azelamide, and N-(5-(((5-(t-butyl) oxazol-2-yl)methyl)thio)thiazol-2-yl)-N'-(1-((2R,4R,5R)-3,3-difluoro-4-hydroxy-5-(hydroxymethyl)tetrahydrofuran-2-yl)-2-oxo-1,2-dihydropyrimidin-4-yl)sebacamide.

* * * * *